(12) United States Patent
Banerjee et al.

(10) Patent No.: US 12,702,516 B2
(45) Date of Patent: Aug. 11, 2026

(54) MOUNTING ENCLOSURE FOR USE WITH A MEDICAL CART

(71) Applicant: Boston Scientific Scimed, Inc., Maple Grove, MN (US)

(72) Inventors: Ankush Banerjee, Minneapolis, MN (US); Christopher John Sperry, Plymouth, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 444 days.

(21) Appl. No.: 18/526,224

(22) Filed: Dec. 1, 2023

(65) Prior Publication Data

US 2024/0180661 A1 Jun. 6, 2024

Related U.S. Application Data

(60) Provisional application No. 63/429,433, filed on Dec. 1, 2022.

(51) Int. Cl.
*A61B 50/13* (2016.01)

(52) U.S. Cl.
CPC .................................... *A61B 50/13* (2016.02)

(58) Field of Classification Search
CPC ...................................................... A61B 50/13
USPC ........................................................... 248/201
See application file for complete search history.

(56) References Cited

U.S. PATENT DOCUMENTS

| | | | | |
|---|---|---|---|---|
| 6,486,399 | B1 * | 11/2002 | Armstrong | H05K 5/0204 439/535 |
| 8,662,605 | B2 * | 3/2014 | McRorie | A61B 50/13 108/50.01 |
| 9,180,898 | B2 * | 11/2015 | Ninomiya | B62B 3/008 |
| 10,792,206 | B2 * | 10/2020 | Soytürk | A61G 12/001 |
| 11,254,340 | B2 * | 2/2022 | Wright | A61G 12/001 |
| 11,415,264 | B2 * | 8/2022 | Bullock | H05K 5/0204 |
| 11,839,048 | B2 * | 12/2023 | Chen | F16B 2/065 |
| 2004/0186357 | A1 * | 9/2004 | Soderberg | A61B 5/681 600/300 |
| 2008/0251661 | A1 * | 10/2008 | Rossini | F16M 11/42 248/176.1 |
| 2010/0148026 | A1 * | 6/2010 | Jang | G06F 1/1607 248/224.8 |
| 2022/0226180 | A1 * | 7/2022 | Lawson | A61B 50/13 |

* cited by examiner

*Primary Examiner* — Anita M King
(74) *Attorney, Agent, or Firm* — Seager, Tufte & Wickhem, LLP

(57) ABSTRACT

Mounting enclosures for use with a medical cart are disclosed. An example mounting enclosure may include a first component having a first base, one or more channel members disposed along the first base, a plurality of hooks, and one or more pole mounting regions. The one or more pole mounting regions may be configured to allow the mounting enclosure to be mounted to a pole of a medical cart. The mounting enclosure may include a second component configured to engage the first component. The second component may have a second base and an angled top surface. The second base may be configured to engage the one or more channel members. A computer compartment may be defined within the mounting enclosure when the first component is engaged with the second component.

20 Claims, 6 Drawing Sheets

22
48
38
51
31
30b
28
39
32
33
34
34
26
30a
36

MOUNTING ENCLOSURE FOR USE WITH A MEDICAL CART

CROSS-REFERENCE TO RELATED APPLICATIONS

This application claims the benefit of priority under 35 U.S.C. § 119 of U.S. Provisional Application No. 63/429,433, filed Dec. 1, 2022, the entire disclosure of which is hereby incorporated by reference.

TECHNICAL FIELD

The present disclosure pertains to medical devices, and methods for manufacturing medical devices. More particularly, the present disclosure pertains to enclosures, for example mounting enclosures, for medical computers.

BACKGROUND

A wide variety of medical devices have been developed for medical use, for example, intravascular use. These devices may be used with medical computers. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device includes a mounting enclosure for use with a medical cart is disclosed. The mounting enclosure comprises: a first component having a first base, one or more channel members disposed along the first base, a plurality of hooks, and one or more pole mounting regions; wherein the one or more pole mounting regions are configured to allow the mounting enclosure to be mounted to a pole of a medical cart; a second component configured to engage the first component, the second component having a second base and an angled top surface; wherein the second base being configured to engage the one or more channel members; and wherein a computer compartment is defined within the mounting enclosure when the first component is engaged with the second component.

Alternatively or additionally to any of the embodiments above, the one or more channel members are defined by arcuate end regions of the first base.

Alternatively or additionally to any of the embodiments above, the first component includes a plurality of pole mounting regions.

Alternatively or additionally to any of the embodiments above, at least some of the plurality of hooks are configured to have a power cord disposed thereon.

Alternatively or additionally to any of the embodiments above, the first component includes a divider.

Alternatively or additionally to any of the embodiments above, the divider defines a tool compartment.

Alternatively or additionally to any of the embodiments above, at least a portion of the angled top surface of the second component extends laterally beyond the first component when the first component is engaged with the second component.

Alternatively or additionally to any of the embodiments above, the second component includes a front panel and wherein at least a portion of the angled top surface of the second component extends laterally beyond the front panel.

Alternatively or additionally to any of the embodiments above, the first component includes a top flange member.

Alternatively or additionally to any of the embodiments above, the top flange member has a non-circular opening formed therein.

A mounting enclosure for use with a medical cart is disclosed. The mounting enclosure comprises: a first component having a first base including a hem; a second component configured to engage the first component, the second component having a second base and an angled top surface; wherein the second base is configured to engage the hem; wherein a computer compartment is defined within the mounting enclosure when the first component is engaged with the second component; and wherein the mounting enclosure to be mounted to a pole-based of a medical cart.

Alternatively or additionally to any of the embodiments above, the first component includes a plurality of pole mounting regions.

Alternatively or additionally to any of the embodiments above, the first component includes a plurality of cord-managing members.

Alternatively or additionally to any of the embodiments above, the first component includes a divider that defines a tool compartment.

Alternatively or additionally to any of the embodiments above, at least a portion of the angled top surface of the second component extends laterally beyond the first component when the first component is engaged with the second component.

Alternatively or additionally to any of the embodiments above, the second component includes a front panel and wherein at least a portion of the angled top surface of the second component extends laterally beyond the front panel.

Alternatively or additionally to any of the embodiments above, the first component includes a top flange member.

Alternatively or additionally to any of the embodiments above, the top flange member has a non-circular opening formed therein.

A mounting enclosure for use with a pole-based medical cart is disclosed. The mounting enclosure comprises: a first component having a first base, a hem region disposed along the first base, a plurality of cord-managing members, and one or more pole mounting regions; a second component configured to engage the first component, the second component having a second base and an angled top surface; wherein the second base being configured to engage the hem region; wherein a computer compartment is defined within the mounting enclosure when the first component is engaged with the second component; and wherein the first component includes a divider that defines a tool compartment adjacent to the computer compartment.

Alternatively or additionally to any of the embodiments above, at least a portion of the angled top surface of the second component extends laterally beyond the first component when the first component is engaged with the second component.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
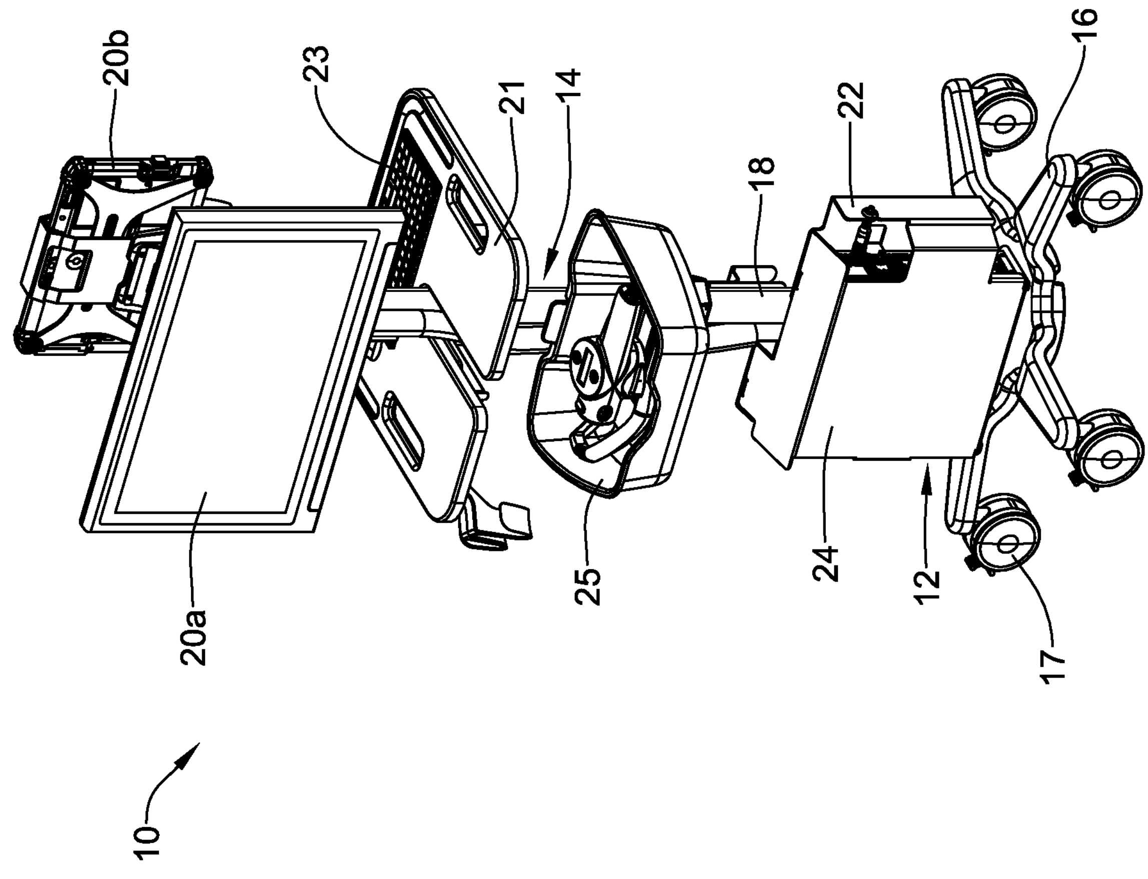
FIG. 1 is a perspective view of an example medical system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Current health care facilities utilize a number of different medical devices and systems. Some of the systems include computers that aid in various interventions. For example, systems like intravascular ultrasound (IVUS) systems may include an IVUS catheter, various tools that work with the catheter, and a computer. It can be appreciated that when some of the systems and/or components of the systems may be capital equipment that is used a number of different times and with a number of different patients. Thus, some systems may utilize a medical cart or the like for these components. For example, a computer for use with and IVUS system may be coupled to a medical cart. The medical cart can be moved to differing locations, depending on where the system is needed. Disclosed herein are enclosures and/or mounting enclosures that may be used with a medical computer. The enclosures may be mounted to a medical cart in a manner that allows for convenient use. Furthermore, the enclosure may include a number of structural features that help improve efficiency of the system, help to shield the computer from fluids while still allowing unimpeded airflow (e.g., cooling airflow), and offer convenient access for cords, cables, accessories, and the like.

FIG. 1 illustrates an example medical cart system 10. The system 10 may include an enclosure 12 and a medical cart/pole assembly 14. The pole assembly 14 may include a base 16 and a pole member 18. In some instances, the base 16 may be stationary base or platform. In other instances, the base 16 may include one or more wheels 17 (and/or the like) so that the pole assembly 14 may be a mobile pole assembly 14. One or more monitors and/or displays 20*a*, 20*b* may be coupled to the pole member 18. In some instances, the display 20*a* may be a monitor. In some of these and in other instances, the display 20*b* may a tablet (e.g., a touch sensitive or touchscreen tablet) or the like. A table or platform 21 may be disposed adjacent to the displays 20*a*, 20*b*. In some instances, the table 21 may include an input device such as a keyboard 23. The pole assembly 14 may include a number of additional components suitable for a variety of medical uses. For example, the pole assembly 14 may include a tray 25 that may be used to house tools and/or accessories for use in a medical intervention.

The enclosure 12 may be a multi-piece assembly including, for example, a first component 22 and a second component 24. In general, the enclosure 12 may be an enclosure suitable for housing a computer or computer system for use with a medical device or system. For example, intravascular ultrasound (IVUS) systems may utilize an IVUS catheter, a motor drive unit, a pullback sled, and a computer (e.g., an acquisition computer). The computer may be considered to be capital equipment that can be used for a number of different interventions and for a number of different patients. As such, it may be desirable for the computer to be housed/protected by the enclosure 12 and associated with a suitable medical assembly/cart such as the pole assembly 14 (e.g., including mobile versions of the pole assembly 14). In some instances, the enclosure 12 may be formed from a suitable material such as a metal or metal alloy (e.g., sheet metal) or a polymer.

Figure 2:
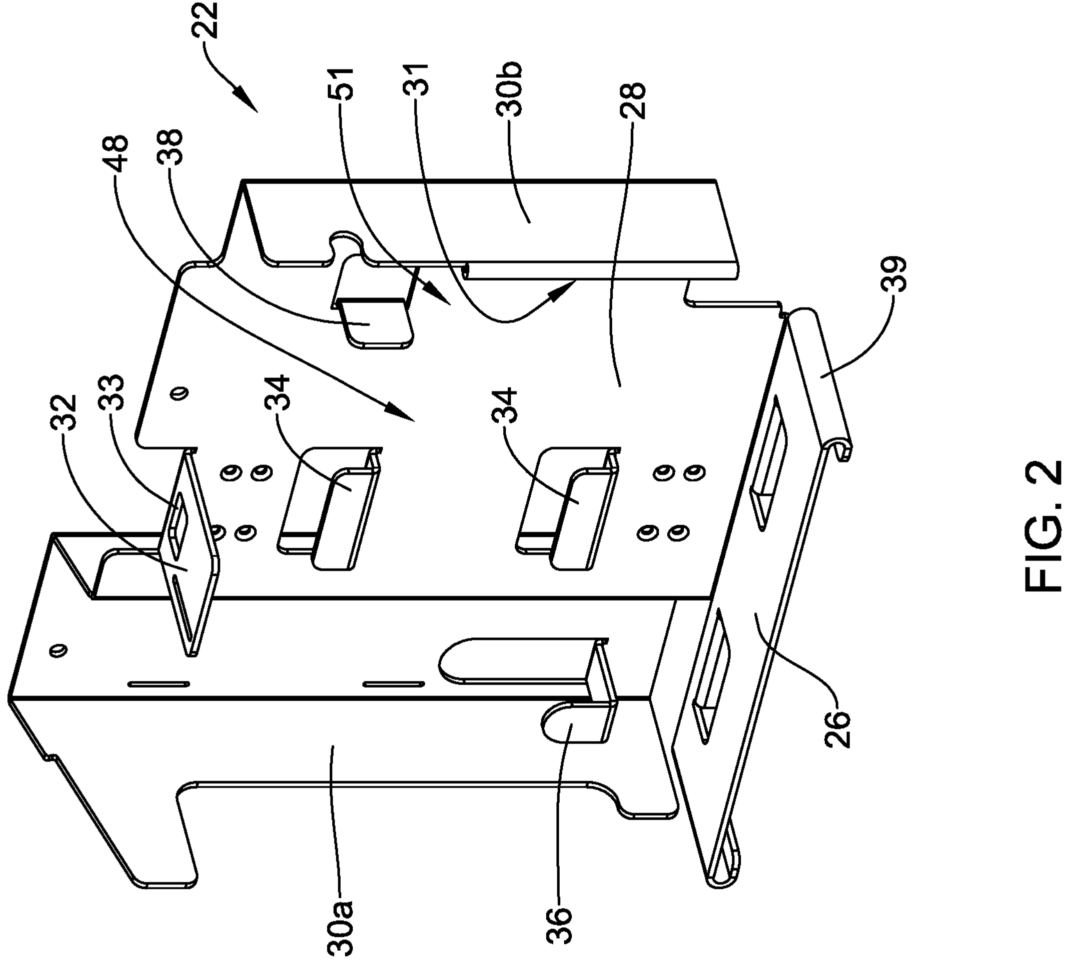
FIG. 2 is a perspective view of a first component of an example enclosure.

FIG. 2 illustrates the first component 22 of the enclosure 12. In at least some instances, the first component 22 may be considered to be the rear or "back" portion of the enclosure. The first component 22 includes a base 26 and a panel 28 (e.g., a rear panel). The base 26 may be suitable for having a computer disposed thereon. One or more side panels such as side panels 30*a*, 30*b* may extend from the panel 28. The side panels 30*a*, 30*b* may be suitable configured/shaped to help engage with the second component 24. For example, the side panel 30*b* may include a side hem or channel region 31.

The first component 22 may include a number of additional structural features including a top flange region 32, one or more hooks 34, a side flange 36, and/or tab/divider 38. The top flange region 32 may be used to help secure the computer within the enclosure 12. In some instances, the top flange region 32 may include an opening 33. The opening 33 provide access for various cords connectors to access the computer. In at least some instances, the opening 33 may be non-circular in shape. For example, the opening 33 may be rectangular in shape. Other shapes are contemplated. The hooks 34 and/or the side flange 36 may help with cord management and may be used to wrap cords (e.g., power cords, etc.) therearound. The flange 36 may also help to hold other devices such as a power supply (e.g., an external power supply) for the medical computer. The tab/divider 38 may help to secure the computer within the enclosure 12. In some instances, the tab/divider 38 may help to divide the interior of the enclosure 12 into a computer compartment or space 48 and a tool/accessory compartment 51. In some instances, the tool/accessory compartment 51 may be used to store accessories such as a power supply and/or the like.

A hem or channel region 39 may be disposed along or adjacent the base 26. The channel region 39, which may be disposed along one side of the base 26 or on opposite sides of the base 26 as shown, may form a connection point or securing region for helping to secure the second component 24 to the first component 22 of the enclosure 12. This may allow for relatively simple connection between the first component 22 and the second component 24 that can be accomplished with only one person. While the connection or channel region 39 is shown as an arcuate hem or channel, other connection arrangements are contemplated.

Figure 3:
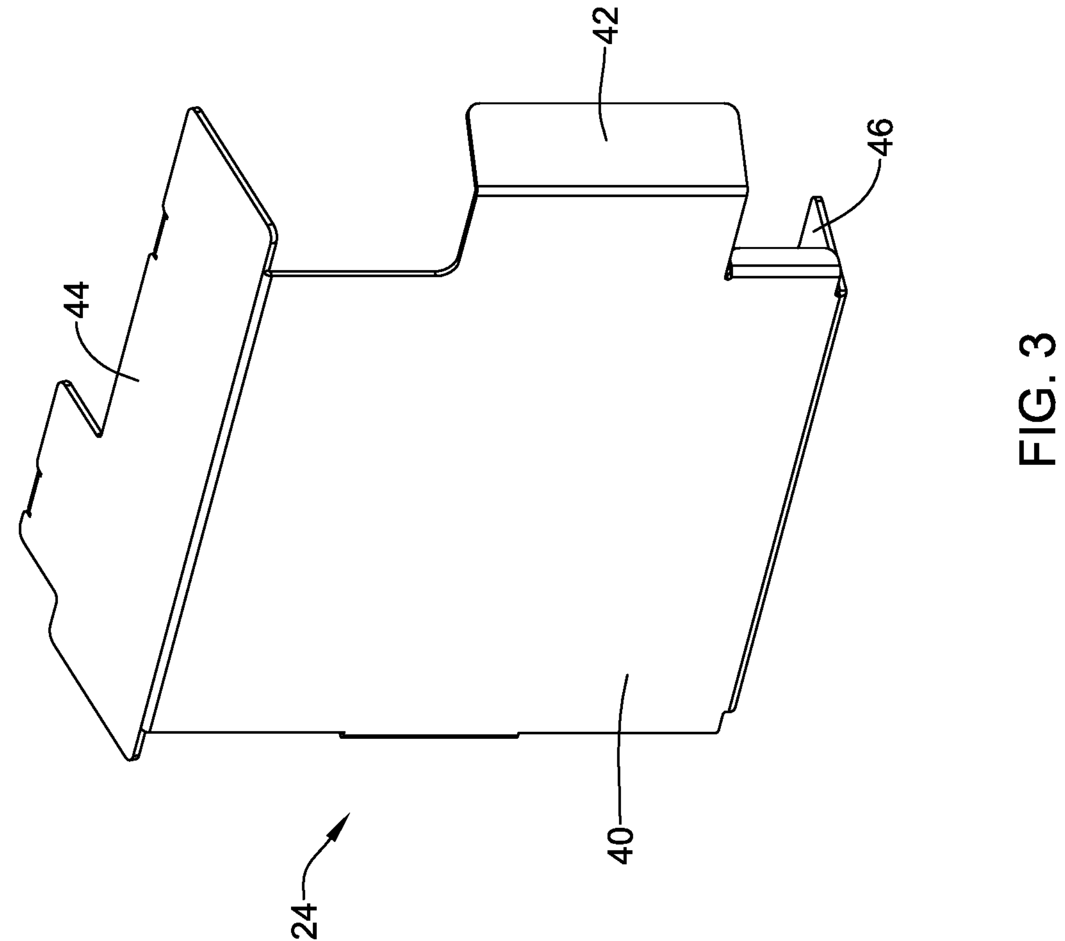
FIG. 3 is a perspective view of a second component of an example enclosure.

FIG. 3 illustrates the second component 24 of the enclosure 12. The second component 24 may include a panel 40 (e.g., a front panel). In some instances, the front panel 40 may provide a surface for product labeling and/or desirable communication to a user. In some of these and in other instances, the front panel 40 may help to conceal as least some of the cords associated with the medical computer and/or allow for easy connection/disconnection of cords. One or more side portions 42 may project from the panel 40. The second component 24 may also include a top portion 44 and a base portion 46. The base portion 46 may be configured to engage the channel region 39 of the first component 22.

The top portion 44 may be angled or slanted (e.g., relative to the ground and/or the base 26) so that, when the second component 24 is engaged with the first component, the top portion 44 may help to divert fluids away from the enclosure 12. This may resemble the angle or pitch of a typical roof or similar structure designed to divert fluid away from the enclosure 12. In some instances, the top portion 44 may be disposed at an angle of 5-60 degrees, or about 15-60 degrees, or about 30-60 degrees, or about 45 degrees. The angle may be measured with respect to the ground (e.g., horizontal) and/or the base 46.

Figure 4:
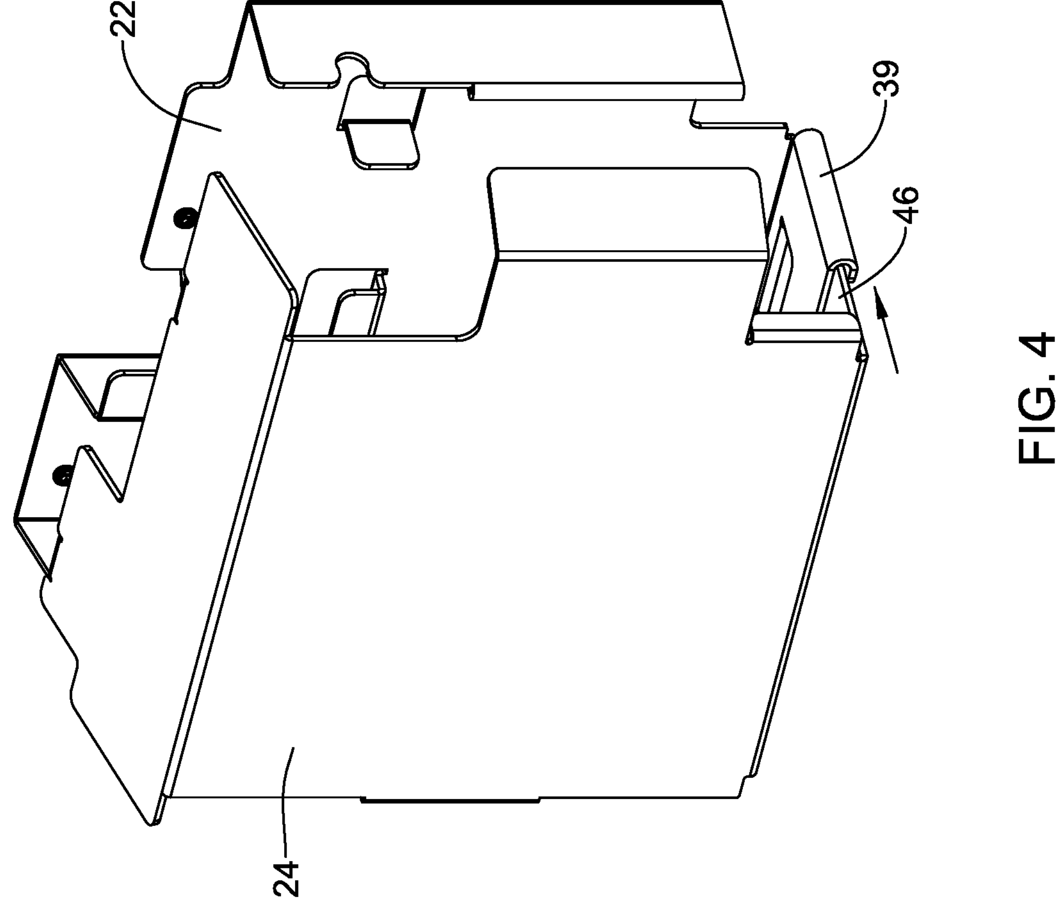
FIG. 4 illustrates the first component of the enclosure and the second component of the enclosure moving into engagement with one another.

FIG. 4 illustrates the first component 22 being engaged with the second component 24. As depicted in FIG. 4, the base 46 of the second component 24 may engage the channel region 39 of the first component. This may help to secure the first component 22 with the second component. In some instances, the engagement between the base 46 with the channel region 39 may include a friction fit that helps to secure the first component 22 with the second component 24. In some of these and in other instances, one or more addition securing members (e.g., screws, bolts, connectors, etc.) may be used to aid the connection between the first component 22 and the second component 24.

Figure 5:
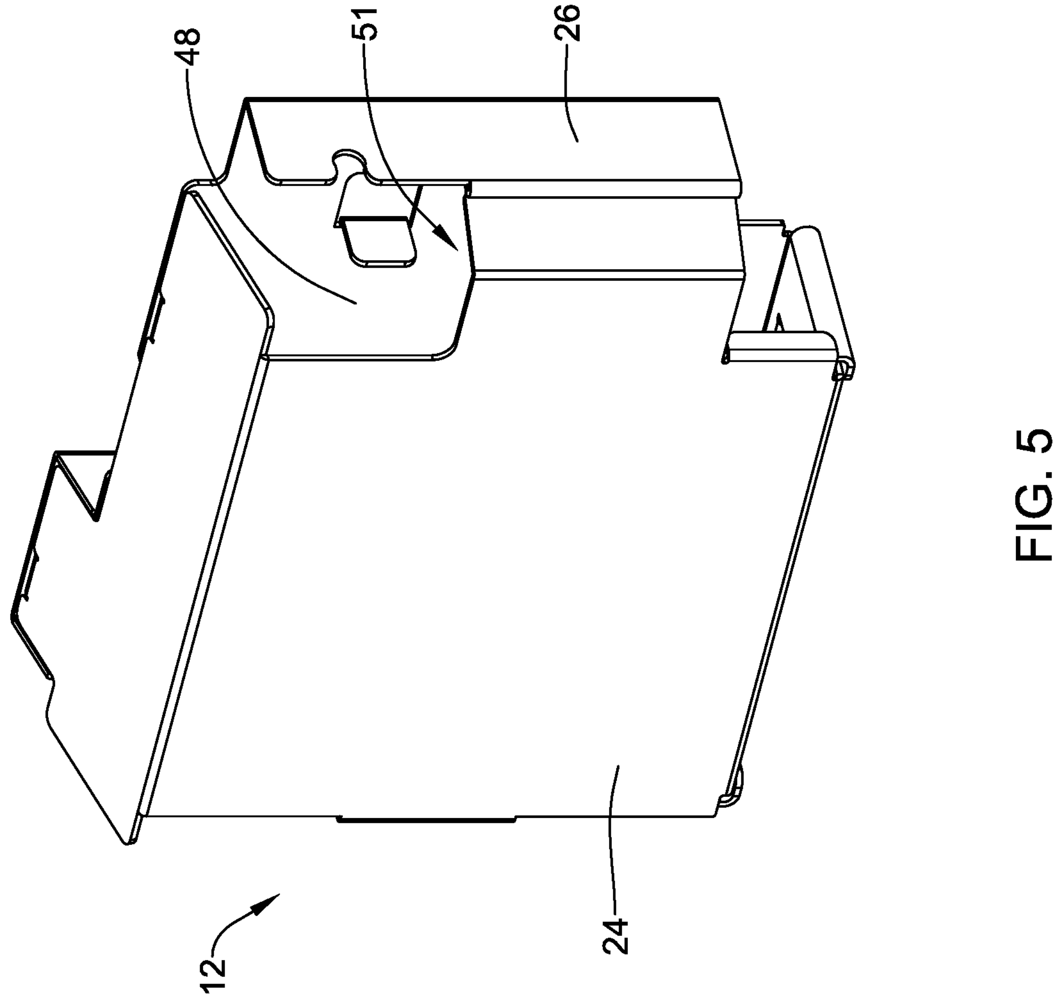
FIG. 5 is a perspective view of an example enclosure.
Figure 6:
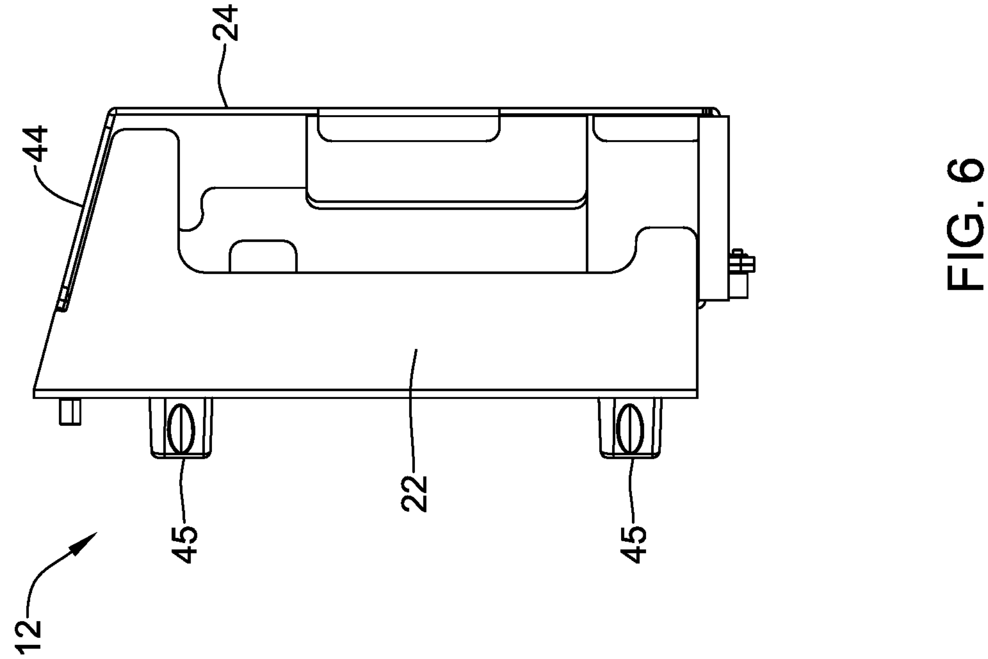
FIG. 6 is a side view of an example enclosure.

FIGS. 5-6 illustrate various view of the enclosure 12. For example, in FIG. 5, it can be seen that the interior of the enclosure 12 generally defines a computer compartment or space 48 suitable for housing a computer. As indicated herein, in some instances, a tool/accessory compartment 51 may also be defined. As can be seen in FIG. 6, the enclosure 12 may include one or more pole mounting regions 45. As the name suggests, the pole mounting regions 45 may be used to mount the enclosure 12 to a pole (e.g., the pole assembly 14). In some instances, the pole mounting regions 45 may be clamps (e.g., C-clamps, O-clamps, split ring clamps, and/or the like) that can be secured to the pole assembly 14. For example, the pole mounting regions may take the form of two halves of a split ring clamp (or similar) that can be brought together to secure the enclosure 12 onto the pole assembly 14. The pole mounting regions 45 may include a screw, bolt, fastener or the like that can secure the pole mounting regions 45 directly to the pole assembly 14 (e.g., by engaging the pole assembly 14). In some of these and in other instances, the fastener may be used to bring opposing halves of the pole mounting regions 45 closer together in order to cause the pole mounting regions 45 to more securely engage the pole assembly 14. Alternatively, the pole mounting regions 45 may take the form of a ring or ring-like structure with a deformable material therein. The deformable material may allow for the pole mounting regions 45 to conform to and/or frictionally engage the pole assembly 14 in a manner that helps to secure the enclosure 12 to the pole assembly 14. In at least some instances, the pole mounting regions 45 may allow for reversible and/or adjustable bonding of the enclosure 12 to the pole assembly 14. This may include allowing the enclosure 12 to be removed and/or adjusted from the pole assembly 14.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A mounting enclosure for use with a medical cart, the mounting enclosure comprising:

a first component having a first base, one or more channel members disposed along the first base, a plurality of hooks, and one or more pole mounting regions;

wherein the one or more pole mounting regions are configured to allow the mounting enclosure to be mounted to a pole of a medical cart;

a second component configured to engage the first component, the second component having a second base and an angled top surface;

wherein the second base being configured to engage the one or more channel members; and wherein a computer compartment is defined within the mounting enclosure when the first component is engaged with the second component.

2. The mounting enclosure of claim 1, wherein the one or more channel members are defined by arcuate end regions of the first base.

3. The mounting enclosure of claim 1, wherein the first component includes a plurality of pole mounting regions.

4. The mounting enclosure of claim 1, wherein at least some of the plurality of hooks are configured to have a power cord disposed thereon.

5. The mounting enclosure of claim 1, wherein the first component includes a divider.

6. The mounting enclosure of claim 5, wherein the divider defines a tool compartment.

7. The mounting enclosure of claim 1, wherein at least a portion of the angled top surface of the second component extends laterally beyond the first component when the first component is engaged with the second component.

8. The mounting enclosure of claim 1, wherein the second component includes a front panel and wherein at least a portion of the angled top surface of the second component extends laterally beyond the front panel.

9. The mounting enclosure of claim 1, wherein the first component includes a top flange member.

10. The mounting enclosure of claim 9, wherein the top flange member has a non-circular opening formed therein.

11. A mounting enclosure for use with a medical cart, the mounting enclosure comprising:

a first component having a first base including a hem;

a second component configured to engage the first component, the second component having a second base and an angled top surface;

wherein the second base is configured to engage the hem;

wherein a computer compartment is defined within the mounting enclosure when the first component is engaged with the second component; and wherein the mounting enclosure to be mounted to a pole-based of a medical cart.

12. The mounting enclosure of claim 11, wherein the first component includes a plurality of pole mounting regions.

13. The mounting enclosure of claim 11, wherein the first component includes a plurality of cord-managing members.

14. The mounting enclosure of claim 11, wherein the first component includes a divider that defines a tool compartment.

15. The mounting enclosure of claim 11, wherein at least a portion of the angled top surface of the second component extends laterally beyond the first component when the first component is engaged with the second component.

16. The mounting enclosure of claim 11, wherein the second component includes a front panel and wherein at least a portion of the angled top surface of the second component extends laterally beyond the front panel.

17. The mounting enclosure of claim 11, wherein the first component includes a top flange member.

18. The mounting enclosure of claim 17, wherein the top flange member has a non-circular opening formed therein.

19. A mounting enclosure for use with a pole-based medical cart, the mounting enclosure comprising:

a first component having a first base, a hem region disposed along the first base, a plurality of cord-managing members, and one or more pole mounting regions;

a second component configured to engage the first component, the second component having a second base and an angled top surface;

wherein the second base being configured to engage the hem region;

wherein a computer compartment is defined within the mounting enclosure when the first component is engaged with the second component; and wherein the first component includes a divider that defines a tool compartment adjacent to the computer compartment.

20. The mounting enclosure of claim 19, wherein at least a portion of the angled top surface of the second component extends laterally beyond the first component when the first component is engaged with the second component.

* * * * *